United States Patent [19]

Hallen et al.

[11] Patent Number: 4,600,529

[45] Date of Patent: Jul. 15, 1986

[54] DEHYDROGENATION OF ALCOHOLS USING ALKALI CARBONATE CATALYSTS

[75] Inventors: Richard T. Hallen, Richland; L. John Sealock, Jr., West Richland, both of Wash.

[73] Assignee: Gas Research Institute, Chicago, Ill.

[21] Appl. No.: 533,851

[22] Filed: Sep. 19, 1983

[51] Int. Cl.$^4$ .............................................. C07C 1/02
[52] U.S. Cl. ..................................... 252/373; 423/651;
423/415 A; 568/403; 568/363; 568/487;
568/485; 585/732; 585/752; 48/179
[58] Field of Search ............... 568/368, 408, 487, 491,
568/485, 403, 363; 48/197 R, 179 R; 252/373;
585/732, 752; 423/651, 415 A

[56] References Cited

U.S. PATENT DOCUMENTS

| | | |
|---|---|---|
| 1,663,350 | 3/1928 | Roka . |
| 1,827,317 | 10/1931 | Jaeger . |
| 1,891,333 | 12/1932 | Meerwein . |
| 1,895,528 | 1/1933 | Taylor . |
| 1,956,088 | 4/1934 | Peski et al. ........................... 568/403 |
| 1,978,404 | 10/1934 | Bloomfield et al. . |
| 2,039,543 | 5/1936 | Lorang . |
| 2,083,877 | 6/1937 | Steck et al. . |
| 2,218,457 | 10/1940 | Winans ................................ 568/403 |
| 2,472,493 | 6/1949 | Schneider et al. . |
| 2,754,181 | 7/1956 | Bond et al. ...................... 423/415 A |
| 2,835,706 | 5/1958 | Cordes . |
| 3,155,730 | 11/1964 | Eng . |
| 3,254,128 | 5/1966 | Hagemeyer et al. ............... 568/485 |
| 3,850,588 | 11/1974 | White .............................. 423/415 A |
| 4,021,370 | 5/1977 | Harris et al. ...................... 48/197 R |
| 4,175,115 | 11/1979 | Ball et al. ........................ 423/415 A |
| 4,182,926 | 1/1980 | Saperstein ........................ 48/197 R |
| 4,348,487 | 9/1982 | Goldstein et al. ................ 48/197 R |
| 4,407,238 | 10/1983 | Yoon .............................. 423/415 A |

FOREIGN PATENT DOCUMENTS 803373 10/1958 United Kingdom .

OTHER PUBLICATIONS

Schwab et al, J.A.C.S., vol. 71, pp. 1806–1816 (1949).
Dent, Chem. Abst., vol. 49, #10605i (1955).
Chem. Abst., vol. 46, #9288e (1952).
Tsutsumi, Chem. Abst., vol. 83, #196,166q, (1975).
Plummer, Catalysts, pp. 1–7 (1982).
The Bureau of Mines Report of Investigations, RI 8013, *Conversion of Cellulosic Wastes to Oil*, (1975).
The Bureau of Mines Report of Investigations, RI 7560, *Converting Organic Wastes to Oil: Replenishable Energy Source*, (1971).
Kraus et al., *Collection Czechoslov. Chem. Commun.*, 40:3856–3860, (1975).

*Primary Examiner*—James H. Reamer
*Attorney, Agent, or Firm*—Klarquist, Sparkman, Campbell, Leigh & Whinston

[57] ABSTRACT

Alkali metal carbonates have been found to be effective catalysts for dehydrogenation of primary and secondary alcohols. The dehydrogenated products may be either predominantly ketones and aldehydes, depending on whether the feed alcohol is secondary or primary, or may be fuel gases. Lower reaction temperatures, in the neighborhood of 600° C., tend to produce high yields of liquid products. Higher temperatures encourage production of fuel gases of high calorific value. When fuel gases are a desired product, a feedstock containing water, in addition to the alcohol, produces increased yields due to the simultaneous catalysis of the water-gas shift reaction.

12 Claims, No Drawings

DEHYDROGENATION OF ALCOHOLS USING ALKALI CARBONATE CATALYSTS

SUMMARY OF THE INVENTION

The present invention is a process for dehydrogenation of primary and secondary alcohols using alkali metal carbonates as catalysts.

Catalytic dehydrogenation of alcohols to corresponding ketones and aldehydes is a process which has been in commercial use for well over fifty years. One major product of this reaction is acetone, produced by catalytically dehydrogenating isopropyl alcohol. Other important products include methyl ethyl ketone and acetaldehyde. Since catalytic dehydrogenation has been such an important chemical process, a large body of knowledge has been built up over the years as scientists have sought to improve the efficiency and selectivity of catalysts.

Catalysts for alcohol dehydrogenation usually fall into a group of materials comprising copper and its alloys such as brass, and oxides of difficultly reducible metals including aluminum, zinc, magnesium, tungsten, titanium, and cerium. These catalysts are usually treated with various promoters to improve selectivity. Common promoters include oxygen-containing compounds of the alkali and alkaline earth metals. The dehydrogenation reaction typically is carried out at temperatures varying between 250° to 500° C. and at relatively low pressures which range from atmospheric to several atmospheres. A good review of the state of the art is found in United Kingdom Pat. No. 803,373.

Reference can be made to the following published documents which appear to be most closely pertinent to the present invention. Taylor et al., in U.S. Pat. No. 1,895,528, teach catalysts which serve either a dehydrogenation or dehydrating function. They found that aluminum and thorium oxides tend toward dehydration, while magnesium oxide was predominantly a dehydrogenating catalyst. Chromium oxides appeared to promote mixed reactions. The inventors noted that the addition of small amounts of alkali or alkaline earth oxides, carbonates, hydroxides, or salts of weak acids exert a marked repressing effect on dehydration reactions. These inventors comment that the effects of the oxide catalyst may be changed by the addition of another substance that may by itself have no catalytic properties, but which will exert a very profound influence on the catalyst in its tendency to repress one or the other reaction. They further comment that these repressers are not to be considered components or constituents of a mixed catalyst, nor are they promoters or activators. In one example, they noted that 4.5% sodium carbonate on zinc oxide drives the dehydrogenation of isopropanol to acetone from 95 mol percent to 99+ mol percent. Other scientists disagree with Taylor et al. and consider the oxygen-containing salts of alkali metals to be promoters.

Van Peski et al., U.S. Pat. No. 1,956,088, note the prior use of small quantities of alkaline compounds as catalysts. These inventors teach a catalyst which consists of a catalytically acting metal or metal oxide on a water-soluble alkaline compound as a carrier. They claim as advantages the reduction of secondary reactions and longer life for their catalyst. Examples include one part of copper oxide on 12.5 parts of sodium carbonate, and one part of copper oxide on 15 parts of potassium carbonate. The inventors clearly consider the carbonate to be an inert or non-catalytic component of the catalyst.

Bloomfield et al., U.S. Pat. No. 1,978,404, teach the use of copper catalysts promoted with oxygen compounds of alkaline earth metals for dehydrogenation and subsequent polymerization of primary alcohols to ketones. Lorang, U.S. Pat. No. 2,039,543, teaches a catalytic process for production of acetone from isopropanol. Sodium carbonate is used as a promoter for a catalyst which, in their case, appears to be copper oxide. In one example, they state that 4 parts sodium carbonate with 20 parts of cupric oxide results in a catalyst having improved conversion efficiency and longer life. Winans, U.S. Pat. No. 2,218,457, teaches the use of alkali metal carbonates as catalyst binders and promoters. The carbonates are said to be advantageous, in that they make the catalysts more resistant to poisoning and more readily reactivated.

Schneider et al., U.S. Pat. No. 2,472,493, teach away from the use of alkali or alkaline earth carbonates and hydroxides as promoters. They note that in instances where these additives have been used, the catalyst is thermally less stable with a reduced life and an increased susceptibility to poisoning. Their preferred catalyst is zinc oxide modified by the addition of a small amount of bismuth oxide. Cordes, U.S. Pat. No. 2,835,706, teaches in the opposite direction and mentions as a preferred dehydrogenation catalyst a composition comprising 92 to 96% zinc oxide, with 4 to 8% sodium carbonate supported on calcined coke. Hagemeyer, Jr., et al., U.S. Pat. No. 3,254,128, teach a complex catalyst for dehydrogenation of primary alcohols to aldehydes. This catalyst is a mixture of predominantly zinc oxide with the oxides of chromium, calcium, magnesium, and aluminum, and also contains a small percentage of potassium sulfate.

Various writers in the general technical literature speak similarly to what is seen above in the patent literature. Most of these articles appear to be syntheses of the work of others for books and papers dealing either with the general subject of catalysis or specific catalytic processes within the chemical process industries. In all of the articles cited, the authors regard oxygen-containing compounds of the alkali metals to be no more than promoters, lacking any catalytic activity in their own right. This fact makes the present discovery that alkali metal carbonates by themselves have high catalytic activity in alcohol dehydrogenation reactions, all the more surprising. This misunderstanding may be in part due to the well known unpredictability of materials having catalytic properties. Kraus et al., *Collection Czechoslov. Chem. Commun.*, 40:3856–3860 (1975) have done a study of the influence of alkali metal compounds on chromium oxide as a dehydrogenation catalyst. They conclude the article by stating "the effect of an alkali metal addition to chromium is complex and not easily predictable on the basis of the knowledge of general properties of an additive".

The following definitions will be pertinent to the present disclosure.

"Active catalyst" means that portion of a catalyst which is effective in promoting the reaction of alcohols to carbonyl compounds and gaseous products which are high in hydrogen. The term excludes such things as inert carriers or supports which serve to present the catalyst in better physical form for reaction.

The terms "catalyst carrier" or "catalyst support" refer to materials which increase the bulk volume and- /or surface area of a catalyst, but which themselves are essentially inert and do not participate in the reaction. Carriers or supports may enhance activity by giving desirable pore distributions and suitable bulk densities. These terms are also meant to include materials which cement small catalyst particles of low mechanical strength into larger geometric forms which are more suitable for use in chemical processes.

"Promoters" are materials which may serve one or more useful functions. They are generally classified as either chemical or structural promoters. Chemical promoters may increase activity of the catalyst, maintain the activity or stability, reduce the tendency to poisoning, and increase the specificity of selectivity of the catalyst by repressing competing reactions. Structural promoters, also known as textural or physical promoters, serve to maintain the physical integrity of the catalytic agent and/or its support material. One way in which they accomplish this purpose is to maintain the true catalyst particles physically separate from each other so that they cannot coalesce or sinter under operating conditions.

The present invention is a process for dehydrogenation of primary or secondary alcohols using alkali metal carbonates as catalysts. This process can be controlled so that, under one set of conditions, the products are predominantly carbonyl compounds. Under modified conditions, the reaction can be controlled so that fuel gases, such as lower alkanes, alkenes, carbon monoxide, and hydrogen are the principal products. The process comprises heating the feed alcohol in the presence of a catalytic amount of an alkali metal carbonate or a mixture of two or more alkali metal carbonates. Surprisingly, the alkali metal carbonates have been found to be highly active catalysts when used by themselves, without any metals or metal compounds from the higher groups of the periodic table being present. All of the alkali metal carbonates have useful catalytic activity, but sodium, potassium, and cesium carbonates are preferred.

The reaction can be directed toward the production of carbonyl compounds with a minimum amount of fuel gases by choosing relatively lower temperatures, lower pressures, and relatively higher throughput rates of the feed alcohol or alcohols through the bed of catalyst.

The dehydrogenation reaction occurs at temperatures of 400° C. and above at atmospheric and higher pressures. The preferred operating temperature at atmospheric pressure is in the range of about 500° to 800° C. Temperatures around 600° C. are preferred when carbonyl compounds are the desired product. Higher temperatures appear to be more useful where the production of fuel gases is the preferred route.

Reactions will normally be carried out in the vapor or gaseous phase.

It is within the scope of the invention either to use the catalyst in an unsupported form or to use it supported on a carrier material. In the latter case, smaller catalyst beds may be necessary since the use of carriers enables the available surface area to be greatly increased.

In one embodiment of the invention, water may be present with the alcohol during the dehydrogenation reaction. The presence of water appears to be a preferred situation where the production of fuel gases is a primary goal. Normally, the amount of water present on a weight basis will not greatly exceed the amount of alcohol in the feed stock.

The process is satisfactory for a wide variety of hydroxylated compounds. It is particularly well adapted for dehydrogenation of aliphatic alcohols, of aromatic compounds where the hydroxyl group is substituted on an alkyl side chain, and for alicyclic alcohols. Feed alcohols which are of particular importance for the production of carbonyl compounds include cyclohexanol and the lower aliphatic alcohols in the range of 2 to 10 carbon atoms. Of particular importance in this latter group are ethanol, 2-propanol, and 2-butanol. The feed materials in this group are dehydrogenated respectively to acetaldehyde, acetone, and methyl ethyl ketone in high yields.

It is an object of the present invention to provide a novel catalyst composition for dehydrogenation of primary and secondary alcohols.

It is another object of this invention to catalytically dehydrogenate primary or secondary alcohols to carbonyl compounds using alkali metal carbonates as the sole catalysts.

It is a further object to provide a process for the production of fuel gases from primary or secondary alcohols using alkali metal carbonates as reaction catalysts.

It is still a further object to provide a selective and highly reactive catalyst for dehydrogenation of primary and secondary alcohols which is very inexpensive.

These and many other objects will become readily apparent to those skilled in the art upon further reading the following detailed description.

DETAILED DESCRIPTION

A laboratory reactor was constructed to demonstrate the efficiency of alkali metal carbonates as dehydrogenation catalysts. The reactor was based on a quartz tube 22 mm in diameter and approximately 200 mm long contained within an electric furnace. The tube was oriented vertically and contained a catalyst bed approximately 9 ml in volume and holding approximately 10 g of catalyst. The contents of the tube were retained by a screen bearing a thin layer quartz wool to support the catalyst. The catalyst was then covered by a heat exchange layer of crushed quartz glass to vaporize incoming liquids and heat the resulting gases to reaction temperature. A thermocouple inserted in the catalyst bed gave an accurate measurement of reaction temperature. Feed materials were introduced into the top of a reaction tube by a metering pump. Reaction products were captured from the gaseous mixture leaving the bottom of the tube. First, the mixture was cooled in an ice water trap at approximately 0° C. backed up by a dry ice trap at approximately −79° C. to condense any liquid products. Any uncondensed gaseous products were captured for measurement and analysis in gas sample bags.

A first series of runs was made using a 50:50 by weight mixture of methanol:water. This mixture was fed to the reactor tube at reaction temperatures of 600° and 800° C. with and without sodium carbonate being present in the reactor. Table I lists the results of this series of experiments and shows the effectiveness of sodium carbonate as a dehydrogenation catalyst.

TABLE I

| Temp. °C. | Catalyst | Feed Rate g/min | Carbon Conversion % | Gas Composition (Vol %) | | | |
|---|---|---|---|---|---|---|---|
| | | | | $H_2$ | CO | $CO_2$ | $CH_4$ |
| 600 | None | 0.46 | 0.8 | 75.8 | 11.2 | 7.0 | 6.0 |

TABLE I-continued

| | Dehydrogenation of Aqueous Methanol[a] | | | | | | |
|---|---|---|---|---|---|---|---|
| Temp. °C. | Catalyst | Feed Rate g/min | Carbon Conversion % | Gas Composition (Vol %) | | | |
| | | | | $H_2$ | CO | $CO_2$ | $CH_4$ |
| 600 | None | 0.92 | 0.3 | 81.2 | 5.7 | 6.7 | 6.9 |
| 600 | $Na_2CO_3$ | 0.46 | 19.2 | 74.0 | 10.4 | 15.3 | 0.3 |
| 600 | $Na_2CO_3$ | 0.96 | 12.5 | 75.1 | 10.6 | 13.6 | 0.7 |
| 800 | None | 0.15 | 67.0 | 63.9 | 33.2 | 1.9 | 0.9 |
| 800 | None | 0.30 | 37.0 | 65.9 | 31.5 | 1.7 | 0.9 |
| 800 | $Na_2CO_3$ | 0.15 | 100.0 | 66.4 | 21.7 | 11.4 | 0.5 |
| 800 | $Na_2CO_3$ | 0.30 | 96.0 | 67.1 | 23.1 | 9.4 | 0.4 |

[a]50:50 by weight methanol

The amount of carbon in the feedstock was compared to the amount of carbon in the liquid products. As shown by the much greater conversion rates, the sodium carbonate is a dehydrogenation catalyst, both at 600° and 800° C. The catalytic effect is best shown by the data at 600° C. where the reduced amount of methane present in the gases indicates that dehydrogenation, rather than thermal cracking, is the principal reaction occurring. It is also probable that some of the water present in the feedstock is being decomposed by the water-gas shift reaction.

While the principal dehydrogenation products of methanol are hydrogen and carbon monoxide, higher alcohols tend to dehydrogenate to either ketones or aldehydes, depending on whether the hydroxyl group is primary or secondary. Another series of runs was made using the same apparatus described previously with 2-propanol being the feedstock. Table II shows the results of this series of experiments. All runs were made at 600° C. using either sodium, potassium, or cesium carbonates as catalyst. The data indicate that conversion percentages increase as the atomic weight of the alkali metal increases. The yield of acetone in the product is less conclusive. The difference between sodium and potassium carbonates, if any, is not well demonstrated. However, either of these materials seems to be more specific to dehydrogenation to acetone than is cesium carbonate.

TABLE II

| | Dehydrogenation of 2-Propanol | | | | |
|---|---|---|---|---|---|
| Run No. | Feed Rate g/min | Catalyst | Carbon Conversion % | Yield %[a] | |
| | | | | Acetone | Gases |
| 1 | 0.29 | $Na_2CO_3$ | 68.2 | 79.7 | 11.6 |
| 2 | 0.39 | $Na_2CO_3$ | 77.3 | 88.7 | 6.8 |
| 3 | 0.79 | $Na_2CO_3$ | 49.5 | 83.4 | 7.0 |
| 4 | 0.39 | $K_2CO_3$ | 72.6 | 81.3 | 11.1 |
| 5 | 0.79 | $K_2CO_3$ | 64.1 | 84.9 | 6.9 |
| 6 | 0.39 | $Cs_2CO_3$ | 88.1 | 68.9 | 23.1 |
| 7 | 0.79 | $Cs_2CO_3$ | 86.9 | 77.0 | 15.1 |

[a]At 600° C., based on carbon in feedstock

Run 2 of the above series was replicated and both liquid and gaseous products were analyzed. A 78% single pass conversion of the alcohol was effected with the principal products being acetone, in 86% mol yield, and acetaldehyde in 3.4% mol yield. The gaseous products comprised 85% hydrogen, 7.7% methane, and 5.1% propylene by volume.

When ethanol was the feedstock at 600° C., with no catalyst present, thermal cracking appeared to be the major reaction occurring, since the gases contained 10.5% ethylene by volume. With a sodium carbonate catalyst present, the off gases contained only 1.7% ethylene with acetaldehyde being a major product. Acetaldehyde was not detected in the experiments without an alkali metal catalyst.

Acetone appears to be relatively stable under the reaction conditions studied, both in the presence and absence of sodium carbonate.

Additional experiments were carried out in which sodium carbonate was supported on Douglas fir charcoal in an amount of approximately 40% by weight of the total material. The supported catalyst was prepared by combining 2.0 g of Douglas fir wood and dry-mixed $Na_2CO_3$, at a concentration of $3.0 \times 10^{-3}$ mole Na/g—Sample, in a stainless steel sample basket. The basket was placed in a pyrolysis reactor wherein the mixture was subjected to steam gasification conditions at 650° C. The resulting char served as the supported catalyst. 10 ml (approximately 0.95 g) of this supported catalyst, containing about 0.4 g of sodium carbonate, was more active than an equivalent volume (10 g) of pure sodium carbonate. The difference is believed due to the much greater of surface area of active catalyst when supported on the char.

While the above examples relate to experiments carried out on lower aliphatic primary and secondary alcohols, alkali metal carbonates are believed to be active dehydrogenation catalysts for all primary and secondary alcohols in which the alcohol is attached to an alkyl chain. Included in this group are also the alicyclic alcohols, such as cyclohexanol and similar cyclic aliphatic materials.

The foregoing descriptions include the best mode known to the inventors of practicing the present invention. It will be apparent to others skilled in the art that many variations can be made in the materials and conditions without departing from the spirit of the invention. The invention is thus considered to be limited only by the following claims.

We claim:

1. A process for dehydrogenation of methanol, which process comprises heating methanol in the presence of a catalytic amount of an active catalyst consisting essentially of an alkali metal carbonate.

2. The process of claim 1 in which water is present during the dehydrogenation reaction.

3. The process of claim 2 in which the dehydrogenation reaction is carried out in the vapor phase.

4. The process of claim 3 in which the pressure is essentially atmospheric.

5. The process of claim 3 in which the pressure is greater than atmospheric.

6. The process of claim 1 in which the reaction temperature is in the range of 500° to 800° C.

7. The process of claim 1 in which the dehydrogenation reaction is carried out in the vapor phase.

8. The process of claim 7 in which the pressure is essentially atmospheric.

9. The process of claim 7 in which the pressure is greater than atmospheric.

10. The process of claim 1 in which the alkali metal carbonate is selected from the group consisting of sodium, potassium, cesium, and mixtures thereof.

11. The process of claim 1 in which the alcohol is dehydrogenated to a mixture of carbonyl compounds and fuel gases.

12. The process of claim 1 in which the catalyst is supported on a carrier.

* * * * *